United States Patent [19]

Maes et al.

[11] 4,095,176

[45] June 13, 1978

[54] METHOD AND APPARATUS FOR EVALUATING CORROSION PROTECTION

[75] Inventors: Jean Pierre Maes, Oostakker; Alan Molyneux, Mariakerke, both of Belgium

[73] Assignee: s.a Texaco Belgium n.v., Brussels, Belgium

[21] Appl. No.: 730,054

[22] Filed: Oct. 6, 1976

[51] Int. Cl.² .......................................... G01R 27/02
[52] U.S. Cl. ........................ 324/65 CR; 204/129.2; 324/29
[58] Field of Search ................. 324/65 R, 65 CR, 29, 324/51, 54, 30 R, 71 E, 57 PS; 204/195 R

[56] References Cited

U.S. PATENT DOCUMENTS

| Re. 26,620 | 7/1969 | Inoue | 204/129.43 |
|---|---|---|---|
| 2,979,444 | 4/1961 | Tiley | 204/129.2 |
| 3,979,666 | 9/1976 | MacLean | 324/30 B |

Primary Examiner—Rudolph V. Rolinec
Assistant Examiner—Michael J. Tokar
Attorney, Agent, or Firm—Thomas H. Whaley; Carl G. Ries; Henry C. Dearborn

[57] ABSTRACT

A method and apparatus for evaluating the corrosion protection that will be provided to a metallic surface by a surface layer. The layer is formed by use of corrosion inhibitors in a corrosive fluid.

11 Claims, 4 Drawing Figures

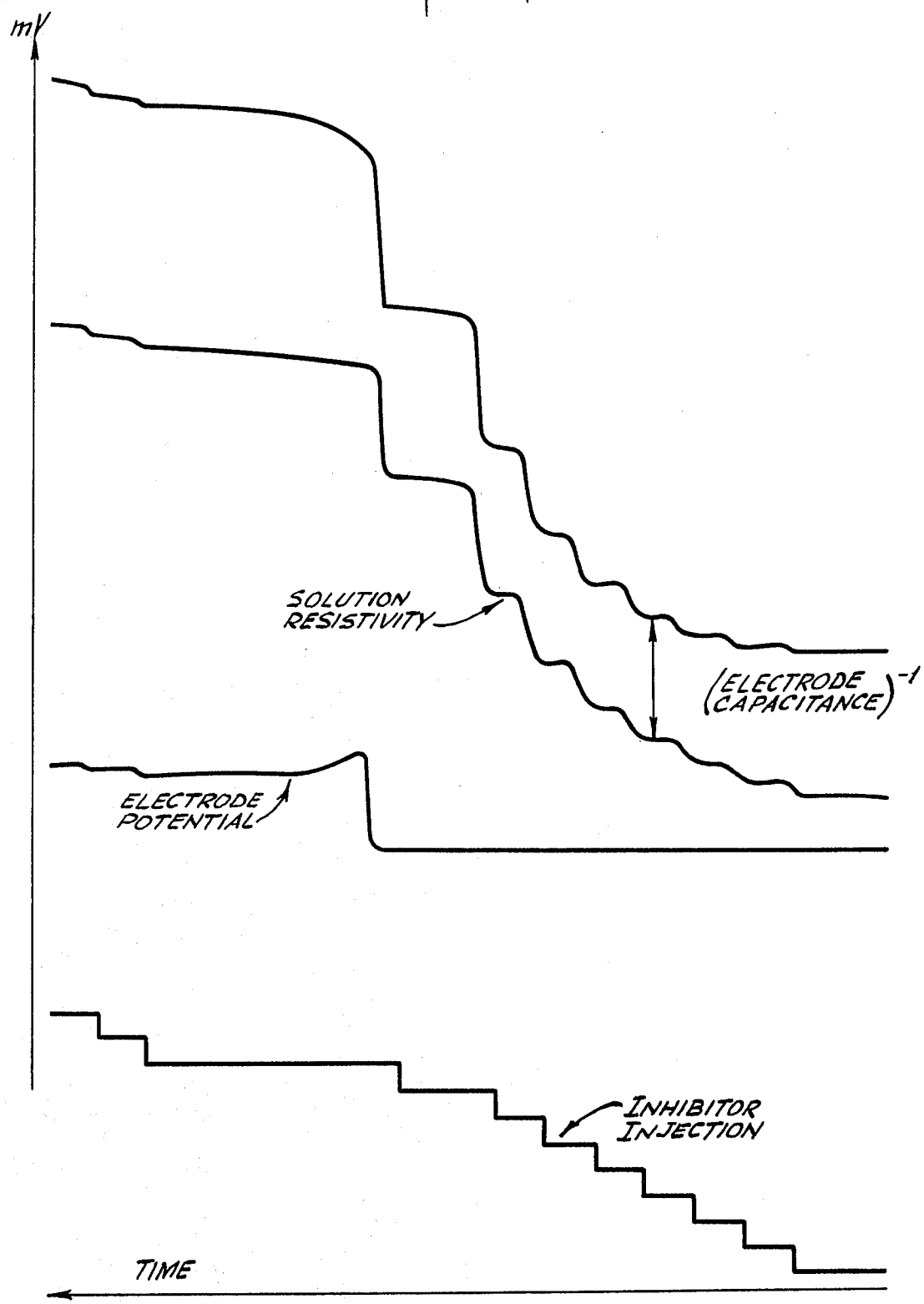

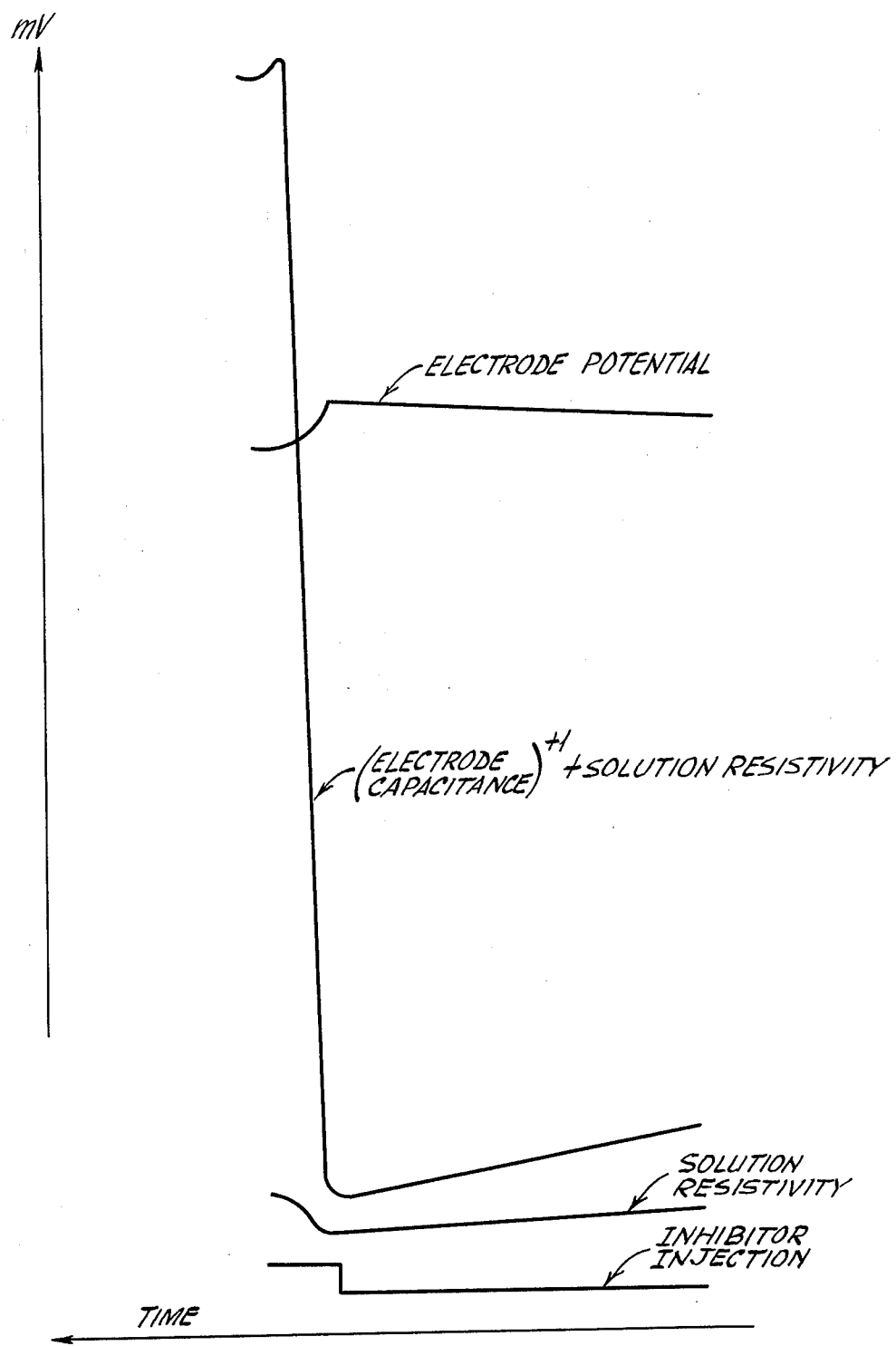

METHOD AND APPARATUS FOR EVALUATING CORROSION PROTECTION

This invention relates to a method of and apparatus for the evaluation of corrosion protection afforded to a metallic surface by a surface layer thereon.

Metallic surfaces are disadvantageously affected by corrosive fluids in many fields of industry. For example, in the petroleum industry, corrosion of metallic surfaces by petroleum materials occurs at all stages of production and distribution. To reduce this corrosion, so-called corrosion inhibitors are often used to a greater or lesser extent. Different inhibitors work in different ways; some by neutralizing active ions, others by reducing ion mobility and others by changing the ion transport numbers. In all cases the electrical conductivity of the corrosive fluid is altered, and various electrical parameters contributing to the overall corrosion mechanism will be affected. Accordingly, by using the corrosive fluid as an electrolyte in which two electrodes are immersed, and by measuring electrical characteristics of the electrolytic circuit, it is possible to derive an indication of any corrosion which continues to occur.

Hitherto, corrosion has been evaluated by measuring the polarisation current. A working electrode (which as used herein means an electrode made of the same metal as that having the surface layer thereon and subject to the same environment) and a measuring electrode of a different metal are immersed in the corrosive fluid (often a third electrode which passes no current is used as a reference electrode), and a D.C. voltage is applied across the two operative electrodes. By correlating potential difference increments against current increments a measure of the polarisation current can be derived.

In practice, the measurement of polarisation current does not necessarily give a reliable evaluation of the protection given to the surface. Although the measurement may indicate very little residual corrosion at the location of the working electrode, it has been found in practice that very substantial corrosion may still be occurring only a short distance away from the working electrode. It is known that, in general, a more reliable evaluation could be obtained by measuring other characteristics of the circuit, such as solution resistivity and electrode capacitance, in addition to polarisation current, but so far no practical method has been devised for effecting these further measurements.

The electrode capacitance, in particular, could be a useful parameter to measure. When a metallic surface is protected by a surface layer against the action of a corrosive fluid, an electrical double-layer structure develops at the interface between the surface and the corrosive fluid. In other words, in a measuring system, a double-layer capacitance is formed at the interface between the working electrode and the corrosive fluid. The value of this capacitance has been found to represent a direct measure of the protection being given to the metallic surface, as distinct from being a measure of the corrosion rate. It is therefore a main object of the present invention to provide an improved method of evaluating corrosion protection afforded to a metallic surface by a surface layer thereon.

According to one aspect of the present invention, there is provided a method of evaluating corrosion protection afforded to a metallic surface by a surface layer thereon, according to which a current path is established through a working electrode and an inert electrode in the corrosive fluid, a pulsed current not exceeding 100 micro-amps and of predetermined frequency not less than 1000 Hz is caused to flow in said circuit path, and the response of said circuit path to the said current flow is measured to determine the solution resistivity and/or the double-layer capacitance at the interface between the working electrode and the corrosive fluid.

According to another aspect of the invention, there is provided apparatus for evaluating corrosion protection afforded to a metallic surface by a surface layer thereon, comprising a working electrode and an inert electrode located in the corrosive fluid, a source of voltage pulses of at least one predetermined frequency not less than 1000 Hz, an impedance through which the source of voltage pulses is connected across the working and inert electrodes to cause a current flow through the corrosive fluid not exceeding 100 micro-amps, and means for measuring the alternating potential difference developed across the working and inert electrodes to determine the solution resistivity and/or the double-layer capacitance at the interface between the working electrode and the corrosive fluid.

It should be understood that, as used herein, the "surface layer" is intended to cover not only films and coatings formed on the metallic surface by the injection of corrosion inhibitors into the corrosive fluid, but also layers which may be applied to the surface by various other known techniques in order to minimize corrosion, and furthermore, protective layers formed by the products of corrosion.

A preferred practical method for evaluating corrosion protection will now be described by way of example with reference to the accompanying drawings, in which:

FIGS. 3 and 4 are graphs showing results obtained by use of the measuring apparatus in cases where the corrosive fluid tested is injected with corrosion inhibitors.

Figure 1:
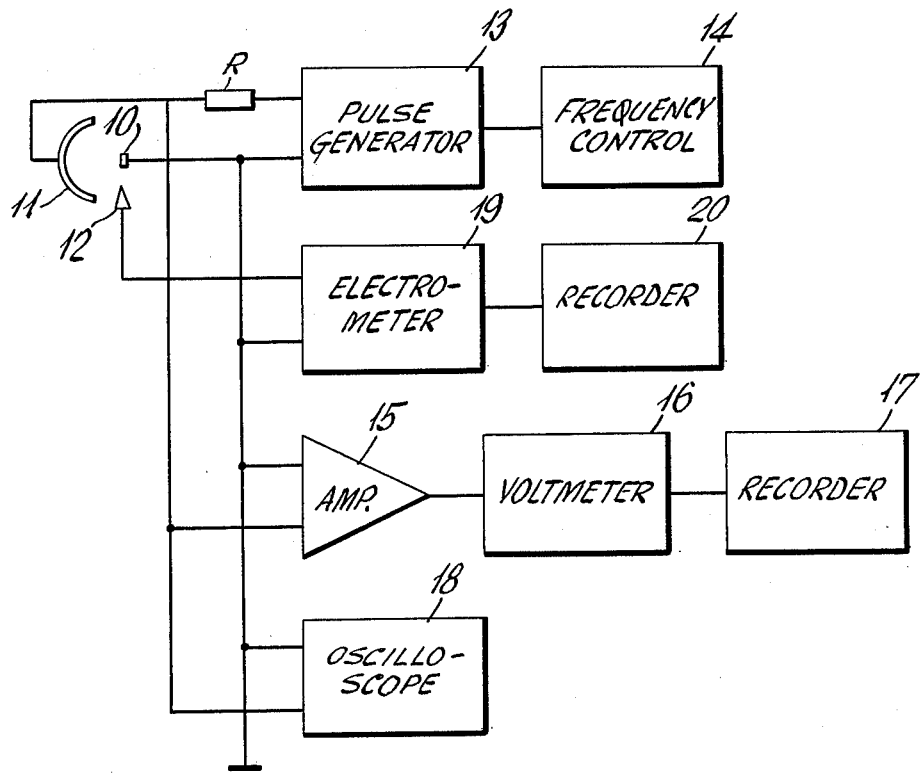
FIG. 1 is a diagram of measuring apparatus including electrodes immersed in the corrosive fluid to form an electrolytic circuit.

The apparatus of FIG. 1 includes three electrodes which, in use, are immersed in the corrosive fluid. In practical applications, the electrodes are embodied in a probe which is inserted into the corrosive fluid through bores in the walls of metallic pipes or containers carrying the corrosive fluid. The corrosive fluid may be constituted, for example, by petroleum products in an oil processing plant, storage unit or distributing equipment. Corrosion protection monitoring may be effected continuously and permanently, or on a periodic and temporary basis.

The three electrodes comprise a working electrode 10 (as hereinbefore defined), an inert electrode 11 (a platinum or other metal electrode inert to the corrosive fluid and the corrosion inhibitors present in the corrosive fluid), and a third electrode 12 (e.g. calomel) which is used solely for measuring polarisation.

Connected across the working and inert electrodes 10, 11 is a pulse generator 13 for producing a pulsed current of relatively high frequency. The pulse generator 13 is connected to a frequency controller 14 which enables the frequency of the pulses generated by the pulse generator to be varied, from say 1000 Hz up to not less than 100 KHz. Included in the circuit line connecting the pulse generator 13 to the inert electrode 11 is a high resistance R having a value predetermined to restrict the magnitude of the pulsed current to a relatively low value not exceeding 100 micro-amps.

Also connected across the working and inert electrodes 10, 11 is an amplifier 15 for amplifying the alternating voltage developed across these two electrodes and applying the amplified output to a voltmeter 16 associated with a recorder 17. An oscilloscope 18 may also be connected across the same two electrodes.

Connected across the working and calomel electrodes 10, 12 is an electrometer 19 associated with a recorder 20, for measuring polarisation potential in accordance with conventional procedures. If desired, a D.C. polarisation voltage may be applied across the working and calomel electrodes to assist polarisation measurements; in this case the pulsed current output of the pulse generator 13 is superimposed on the D.C. polarisation voltage.

As previously explained, when a metallic surface is protected by a surface layer, as by the injection of corrosion inhibitors into the corrosive fluid, a double-layer capacitance is formed at the interface between the metallic surface, i.e. the working electrode of the measuring system, and the corrosive fluid. At high frequencies, i.e. exceeding 1000 Hz, the circuit diagram of FIG. 2 constitutes an electrical circuit equivalent to the electrolytic circuit formed by the electrodes 10, 11. From this equivalent circuit a mathematical model can be developed.

Figure 2:
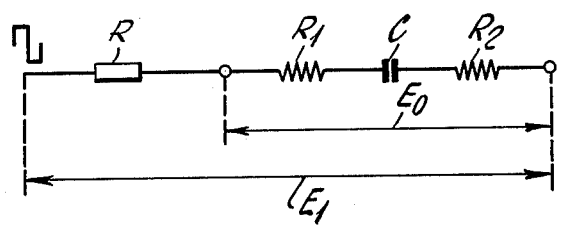
FIG. 2 is an electrical circuit diagram equivalent to the electrolytic circuit shown in FIG. 1.

The response in time $(t)$ of the circuit of FIG. 2 to a voltage amplitude change $(\Delta V)$ will be:

$$E_o(t) = \Delta V \frac{R_1 + R_2}{R + R_1 + R_2} \cdot e^{-\frac{t}{(R+R_1+R_2)c}} +$$

$$\Delta V \left[ 1 - e^{-\frac{t}{(R+R_1+R_2)C}} \right],$$

where $R_1$ is the solution resistance, $R_2$ is the total lead resistance, R is the series resistance through which high frequency pulses are applied to the electrodes, C is the double-layer capacitance, and $E_o$ is the voltage developed across the electrodes 10, 11 in response to the change $\Delta V$ in the applied voltage $E_1$.

When an alternating pulse of amplitude $(\Delta V)$ and duration $(\Delta t)$ is applied to the electrolytic cell, the average potential difference developed at the output is:

$$E_o = \Delta V \frac{R_1 + R_2}{R + R_1 + R_2} \cdot e^{-\frac{\Delta t}{(R+R_1+R_2)C}} +$$

$$\frac{\Delta V}{4} \left[ 1 - e^{-\frac{\Delta t}{(R+R_1+R_2)C}} \right]$$

Assuming that the total lead resistance ($R_2$) is much smaller than the solution resistance ($R_1$), that the solution resistance is much smaller than the series resistance (R), and that at the high pulse frequency chosen $\Delta t$ is much less than $(R+R_1+R_2)C$, the last equation reduces to:

$$E_o = \frac{\Delta V}{R} \cdot R_1 + \frac{\Delta V}{4R} \cdot \frac{\Delta t}{C}.$$

The first term in this simplified equation is due to the contribution of solution resistance ($R_1$) and is independent of pulse frequency. The second term is related to the double-layer capacitance (C).

By changing the frequency generated by the pulse generator 13, the two terms can be separated. At very high frequencies (of the order of 100 KHz or higher), the contribution of the second term is negligible (because $\Delta t$ is small) and the output voltage is proportional to solution resistance. As the generated frequency is reduced down to 1000 Hz, the voltage output includes both solution resistance and double-layer capacitance, with the latter contribution becoming dominant. At 1000 Hz the output voltage is essentially a measure of the double-layer capacitance.

The simplified equation holds with accuracy only for frequencies in excess of 1000 Hz and a high value of R sufficient to reduce the current magnitude to 100 micro-amps or less.

Thus according to the mathematical model, electrode capacitance and solution resistance can be measured by means of the voltmeter 16 and recorder 17, and/or the oscilloscope 18, when a pulsed current not exceeding 100 micro-amps and of frequency not less than 1000 Hz is applied to the electrolytic cell by means of the frequency-controlled pulse generator 13.

The measured solution resistance is related to solution resistivity (Ps) of the electrolyte by the equation:

$$R_1 = Ps \frac{d}{S},$$

where S is the area of the effective exposed electrode surface and (d) the distance between the working and inert electrodes 10, 11.

The validity of the mathematical model has been checked by measurements made on a standard electrolytic cell, employing a Monel alloy electrode as the working electrode and a standard hydrochloric acid solution as the corrosive fluid. The measured circuit response closely corresponds with that derived theoretically by electronic circuit analysis based on the mathematical model in question.

FIG. 3 shows a set of graphs for the recorded electrode potential (indicative of polarisation), solution resistivity and reciprocal of the double-layer capacitance, when the apparatus is employed to monitor a Monel alloy electrode subject to the corrosive effect of hydrochloride acid solution, during a period in which doses of a corrosion inhibitor (morpholine) are successively injected. Capacitance and resistivity measurements have been separated by changing the input frequency from 10 KHz to 100 KHz.

After each morpholine injection, solution resistivity increases. Neutralisation point of the acid solution is marked by an instantaneous jump of electrode potential, followed by a change to the more noble direction, while electrode capacitance is decreasing.

The changes in electrode capacitance and electrode potential are attributable to changes in ion-activities and ion-mobilities in the solution, rather than film-forming properties of morpholine on the Monel alloy.

FIG. 4 shows a similar set of graphs resulting from the monitoring of a Monel alloy electrode in an aqueous hydrocarbon mixture during film-forming produced by steady addition of a corrosion inhibitor.

Ten-fold reduction of electrode capacitance indicates that an inhibitor film is formed after addition of a specific amount of inhibitor. The degree of protection is indicated by the change of electrode potential to the more noble direction. There is relatively small change in solution resistivity.

In the cases illustrated in FIGS. 3 and 4, inhibition of electrode reaction due to injection of a corrosion inhibitor is indicated by the change in electrode potential (polarisation current), but instances may often occur when inhibition is achieved even though change in polarisation current is not observed. Measurements of solution resistivity and/or electrode capacitance are essential in these instances, in addition to being valuable in all cases as a measure of the protection achieved, as distinct from the measure of residual corrosion which is indicated by polarisation current.

For relatively thick inhibition films, the following equation is applicable:

$$C = \epsilon_1 \frac{S}{t_f}$$

where $\epsilon_1$ is the dielectric constant of the inhibitor and $t_f$ is the film thickness. As before, S is the area of the effective exposed electrode surface. Corrosion protection is not only a function of film thickness, and in this case it is important to take solution resistivity measurements into account, in addition to measurements of polarisation current. It is also to be noted that measurement of solution resistivity is important for dilute solutions. In general, however, as can be noted from FIG. 4, the measurement of the double-layer capacitance is of prime importance to achieve a reliable indication of corrosion protection.

What we claim is:

1. A method of evaluating corrosion protection afforded to a metallic surface by a surface layer thereon, wherein said metallic surface is contacted by a corrosive fluid, comprising the steps of establishing a circuit path through a working electrode and an inert electrode in the corrosive fluid, causing a pulsed current not exceeding 100 micro-amps and of predetermined frequency not less than 100 Hz to flow in said circuit path, and measuring the response of said circuit path to the said current flow to determine the solution resistivity and the double-layer capacitance at the interface between said working electrode and the corrosive fluid.

2. A method according to claim 1, wherein said pulsed current includes a second predetermined frequency higher than that of the first-mentioned pulsed current, and wherein the response of said circuit path to the higher frequency current flow is measured to isolate solution resistivity measurements from electrode capacitance measurements.

3. A method according to claim 2, wherein the circuit response is continuously monitored.

4. A method according to claim 3, wherein the circuit response is monitored by amplifying and recording the alternating potential difference developed across the working and inert electrodes.

5. A method according to claim 4, wherein the circuit response is also monitored by an oscilloscope.

6. A method according to claim 2, wherein the higher predetermined frequency is at least 10 times the first-mentioned predetermined frequency.

7. A method according to claim 6, wherein the first-mentioned predetermined frequency is not more than 10 KHz and the higher predetermined frequency is not less than 100 KHz.

8. Apparatus for evaluating corrosion protection afforded to a metallic surface by a surface layer thereon, wherein said metallic surface is contacted by a corrosive fluid, comprising in combination a working electrode and an inert electrode located in the corrosive fluid, a source of voltage pulses of at least one predetermined frequency not less than 1000 Hz, an impedance through which the source of voltage pulses is connected across said working and inert electrodes to cause a current flow through the corrosive fluid not exceeding 100 micro-amps, and means for measuring the alternating potential difference developed across said working and inert electrodes to determine the solution resistivity and the double-layer capacitance at the interface between said working electrode and the corrosive fluid.

9. Apparatus according to claim 8, wherein the measuring means comprises a voltmeter and a continuous recorder.

10. Apparatus according to claim 8, wherein a third electrode is located in the corrosive fluid for simultaneous measurement of polarization current.

11. Apparatus according to claim 9, wherein a third electrode is located in the corrosive fluid for simultaneous measurement of polarization current.

* * * * *